United States Patent
Baillot

(10) Patent No.: US 9,323,055 B2
(45) Date of Patent: Apr. 26, 2016

(54) SYSTEM AND METHOD TO DISPLAY MAINTENANCE AND OPERATIONAL INSTRUCTIONS OF AN APPARATUS USING AUGMENTED REALITY

(75) Inventor: Yohan Baillot, Reston, VA (US)

(73) Assignee: Exelis, Inc., McLean, VA (US)

(*) Notice: Subject to any disclaimer, the term of this patent is extended or adjusted under 35 U.S.C. 154(b) by 460 days.

(21) Appl. No.: 11/441,241

(22) Filed: May 26, 2006

(65) Prior Publication Data

US 2007/0273610 A1    Nov. 29, 2007

(51) Int. Cl.
| G09G 5/00 | (2006.01) |
| G02B 27/01 | (2006.01) |
| G06F 3/01 | (2006.01) |
| G06F 3/03 | (2006.01) |
| G06F 3/0346 | (2013.01) |
| G08G 5/00 | (2006.01) |
| A61B 19/00 | (2006.01) |

(52) U.S. Cl.
CPC .............. *G02B 27/017* (2013.01); *G06F 3/011* (2013.01); *G06F 3/0325* (2013.01); *G06F 3/0346* (2013.01); *G08G 5/0021* (2013.01); *G08G 5/0069* (2013.01); *A61B 2019/5229* (2013.01); *A61B 2019/5291* (2013.01); *G02B 2027/0138* (2013.01); *G02B 2027/0187* (2013.01)

(58) Field of Classification Search
USPC .................................. 345/7, 8; 356/620, 623
See application file for complete search history.

(56) References Cited

U.S. PATENT DOCUMENTS

| 5,506,862 | A | 4/1996 | McIntosh |
| 6,064,335 | A | 5/2000 | Eschenbach |
| 6,112,015 | A * | 8/2000 | Planas et al. .................. 709/223 |
| 6,166,744 | A | 12/2000 | Jaszlics et al. |
| 6,281,790 | B1 | 8/2001 | Kimmel et al. |
| 6,348,877 | B1 | 2/2002 | Berstis et al. |
| 6,434,416 | B1 | 8/2002 | Mizoguchi |
| 6,453,168 | B1 | 9/2002 | McCrady et al. |

(Continued)

FOREIGN PATENT DOCUMENTS

| DE | 19639615 | 4/1998 |
| EP | 0899690 | 3/1999 |

(Continued)

OTHER PUBLICATIONS

"Microvision: Applications", printed from http://www.microvision.com/apps.html, May 10, 2006, 1 page.

(Continued)

*Primary Examiner* — Calvin C Ma
(74) *Attorney, Agent, or Firm* — Davidson Berquist Jackson & Gowdey LLP

(57) ABSTRACT

A head-mounted display provides a user with an augmented view of an object being viewed; a tracking mechanism such as a camera repeatedly determine the position and orientation of the head-mounted display relative the object being viewed; and a computer system provides information for the augmented view and repeatedly updates the augmented view of the object being viewed based on the determined position and orientation of the display. The head-mounted display may be a see-through display; it may be video-based or optical-based, and it may be monoscopic and stereoscopic. The tracking mechanism determines its position using one or more markers or beacons on the object being viewed. The markers may be active or passive, including light-emitting diodes (LEDs) that emit invisible light.

26 Claims, 3 Drawing Sheets

(56) References Cited

U.S. PATENT DOCUMENTS

| | | | |
|---|---|---|---|
| 6,466,232 | B1 | 10/2002 | Newell et al. |
| 6,474,159 | B1 | 11/2002 | Foxlin et al. |
| 6,500,008 | B1 | 12/2002 | Ebersole et al. |
| 6,587,809 | B2 | 7/2003 | Majoe |
| 6,607,038 | B2 | 8/2003 | Ebersole et al. |
| 6,616,454 | B2 | 9/2003 | Ebersole et al. |
| 6,653,990 | B1 | 11/2003 | Lestruhaut |
| 6,675,091 | B2 * | 1/2004 | Navab .................. 701/207 |
| 6,708,142 | B1 | 3/2004 | Baillot et al. |
| 6,757,068 | B2 | 6/2004 | Foxlin |
| 6,809,743 | B2 | 10/2004 | Ebersole et al. |
| 6,809,744 | B2 | 10/2004 | Ebersole et al. |
| 6,853,972 | B2 | 2/2005 | Friedrich et al. |
| 6,856,324 | B2 | 2/2005 | Sauer et al. |
| 6,889,192 | B2 | 5/2005 | Friedrich et al. |
| 6,903,707 | B2 | 6/2005 | Hobgood et al. |
| 6,922,632 | B2 | 7/2005 | Foxlin |
| 6,962,277 | B2 | 11/2005 | Quintana et al. |
| 6,989,831 | B2 | 1/2006 | Ebersole et al. |
| 7,002,551 | B2 | 2/2006 | Azuma et al. |
| 7,046,214 | B2 | 5/2006 | Ebersole et al. |
| 7,071,898 | B2 | 7/2006 | Hobgood et al. |
| 7,110,013 | B2 | 9/2006 | Ebersole et al. |
| 7,126,558 | B1 | 10/2006 | Dempski |
| 7,138,963 | B2 | 11/2006 | Hobgood et al. |
| 7,215,322 | B2 * | 5/2007 | Genc et al. ................ 345/157 |
| 7,245,273 | B2 * | 7/2007 | Eberl et al. .................. 345/7 |
| 7,324,081 | B2 | 1/2008 | Friedrich et al. |
| 7,849,421 | B2 | 12/2010 | Yoo et al. |
| 8,217,856 | B1 | 7/2012 | Petrou |
| 2002/0008153 | A1 | 1/2002 | Ebersole et al. |
| 2002/0039085 | A1 | 4/2002 | Ebersole et al. |
| 2002/0044104 | A1 | 4/2002 | Friedrich et al. |
| 2002/0069072 | A1 | 6/2002 | Friedrich et al. |
| 2002/0074370 | A1 | 6/2002 | Quintana et al. |
| 2002/0101568 | A1 | 8/2002 | Eberl et al. |
| 2002/0140694 | A1 | 10/2002 | Sauer et al. |
| 2002/0140708 | A1 | 10/2002 | Sauer et al. |
| 2002/0140709 | A1 | 10/2002 | Sauer et al. |
| 2002/0160343 | A1 | 10/2002 | Ebersole, Jr. et al. |
| 2002/0174367 | A1 | 11/2002 | Kimmel et al. |
| 2002/0191003 | A1 | 12/2002 | Hobgood et al. |
| 2002/0197591 | A1 | 12/2002 | Ebersole et al. |
| 2003/0003430 | A1 | 1/2003 | Ebersole et al. |
| 2003/0017438 | A1 | 1/2003 | Ebersole et al. |
| 2003/0037449 | A1 | 2/2003 | Bani-Hashemi |
| 2003/0040914 | A1 | 2/2003 | Friedrich et al. |
| 2003/0050785 | A1 | 3/2003 | Friedrich et al. |
| 2004/0080467 | A1 | 4/2004 | Chinthammit et al. |
| 2004/0105427 | A1 | 6/2004 | Friedrich et al. |
| 2004/0113885 | A1 | 6/2004 | Genc et al. |
| 2004/0149036 | A1 * | 8/2004 | Foxlin et al. ................ 73/511 |
| 2004/0201857 | A1 * | 10/2004 | Foxlin ..................... 356/620 |
| 2004/0212630 | A1 | 10/2004 | Hobgood et al. |
| 2005/0093889 | A1 | 5/2005 | Sauer et al. |
| 2005/0168403 | A1 | 8/2005 | Ebersole et al. |
| 2005/0177375 | A1 | 8/2005 | Friedrich et al. |
| 2005/0195279 | A1 | 9/2005 | Hobgood et al. |
| 2005/0203380 | A1 | 9/2005 | Sauer et al. |
| 2005/0232499 | A1 | 10/2005 | Ha et al. |
| 2005/0256396 | A1 | 11/2005 | Takemoto |
| 2006/0043314 | A1 * | 3/2006 | Katzir et al. ................ 250/484.5 |
| 2006/0075356 | A1 | 4/2006 | Faulkner et al. |
| 2007/0018880 | A1 | 1/2007 | Huston |
| 2007/0276590 | A1 | 11/2007 | Leonard et al. |
| 2008/0204361 | A1 | 8/2008 | Scales et al. |

FOREIGN PATENT DOCUMENTS

| | | |
|---|---|---|
| EP | 01772110 | 4/2007 |
| JP | 07-056624 | 3/1995 |
| JP | 2000-102036 | 4/2000 |
| JP | 2002-032784 | 1/2002 |
| JP | 2002-278670 | 9/2002 |
| JP | 2003-337963 | 11/2003 |
| JP | 2004-538538 | 12/2004 |
| JP | 2005-520441 | 7/2005 |
| JP | 2005-351886 | 12/2005 |
| JP | 2009-538487 | 11/2009 |
| WO | WO 99/05580 | 2/1999 |
| WO | WO 2006/053185 | 5/2006 |

OTHER PUBLICATIONS

"Microvision: Benefits & Features", printed from http://www.microvision.com/nomad_benefits.html, May 10, 2006, 2 pages.

"Microvision: Nomad Display Systems", printed from http://www.microvision.com/nomad.html, May 10, 2006, 1 page.

Feiner, Steven et al., "Augmented Reality for Construction", printed from http://www1.cs.columbia.edu/graphics/projects/arc/arc.html, (Date Unknown), pp. 1-5.

Feiner, Steven et al., "KARMA Knowledge-Based Augmented Reality for Maintenance Assistance", printed from http://www1.cs.columbia.edu/graphics/projects/karma/karma.html, (Date Unknown), pp. 1-2.

Foxlin, Eric et al., "VIS-Tracker: A Wearable Vision-Inertial Self-Tracker", IEEE VR2003, Mar. 22-26, 2003, Los Angeles, 8 pages.

Foxlin, Eric, "Generalized Architecture for Simultaneous Localization, Auto-Calibration, and Map-Building", IEEE/RSJ Conf. on Intelligent Robots and Systems (IROS 2002), Oct. 2-4, 2002, 7 pages.

Hildebrand, Axel et al., "Archeoguide: An Augmented Reality Based System for Personalized Tours in Cultural Heritage Sites", printed from http://archeoguide.intranet.gr/publications.htm, (Date Unknown), 10 pages.

Starner, T., Mann, S., Rhodes, B., Levine, J., Healey, J., Kirsch, D., Picard, R. W., Pentland, A., "Augmented Reality Through Wearable Computing", M.I.T. Media Laboratory Perceptual Computing Section Technical Report No. 397, 1997, pp. 1-9.

"Boeing Applied Research & Development, M&CT Technology Foucs", Boeing: Mathematics and Computing Technology—Technology Focus, printed from http://www.boeing.com/assocproducts/art/tech_focus.html on.

"Boeing", printed from http://ovrt.nist.gov/projects/mfg/mfg_cs_boeing.html on Mar. 30, 2006 (2 pp.).

"NOMAD Expert Technician System" (2004), Microvision, www.microvision.com/nomad (2 pp.).

Azuma R., Baillot Y., Feiner S., Julier S., MacIntyre B., Reinhold B. (2001) "Recent Advances in Augmented Reality", IEEE CG&A.

Baillot Y, Gagas E, Höllerer T, Julier S, Feiner S (2000) "Wearable 3D graphics for augmented reality: a case study of two experimental backpack computers", NRL Technical Report.

Baillot Y., Brown D., Julier S. (2001) "Authoring of Physical Models Using Mobile Computers", ISWC2001, Zurich, Oct. 2001.

Baillot Y., Eliason J., Schmidt G., Swan E., Brown D., Julier S., Livingston M., Rosenblum L. (2003) "Evaluation of the ShapeTape tracker for Wearable, Mobile Interaction", VR2003, Los Angeles, Mar. 2003.

Baillot Y., Julier S., Brown D., Livingston M. (2003) "A Tracker Aligninent Framework for Augmented Reality", ISMAR 2003, Tokyo, Oct. 2003.

Baillot, Y (1998) "First Implementation of the Virtual Reality Dynamic Anatomy (VRDA) tool", Master thesis dissertation, School of Computer Sciences, University of Central Florida.

Baillot, Y (1999) "Study on spherical tracking probes design", CREOL/UCF, Technical Report 99-01.

Baillot, Y., & Rolland, J. (1996) "Fundamental principles of tracking technology for virtual environments", CREOL/UCF, Technical Report 96-04.

Baillot, Y., & Rolland, J. (1996) "Improvement of an Augmented Reality Bench Prototype", Engineering degree final report, CREOL/UCF, Technical Report 96-01.

Baillot, Y., J.P. Rolland, K. Lin, and D.L. Wright (2000) "Automatic modeling of knee-joint motion for the virtual reality dynamic anatomy (VRDA) tool" Presence: Tele operators and Virtual Environments (MIT Press) 9(3), 223-235.

(56) References Cited

OTHER PUBLICATIONS

Baillot, Y., Rolland, J.P., & Wright, D.L. (1999) "Automatic Modeling of knee-joint motion for the Virtual Reality Dynamic Anatomy Tool (VRDA)", Proceedings of Medicine Meets Virtual Reality 99, IOS Press.
Brown D., Baillot Y., Bailey M.P., Pfluger K.C., Maassel P., Thomas J., Julier S. "Using Augmented Reality to Enhance Fire Support Team Training", I/ITSEC 2005, Orlando, FL, Dec. 2005.
Brown D., Baillot Y., Julier S., Armoza D., Eliason J., Livingston M., Rosenblum L., Garrity P. (2003) "Data Distribution for Mobile Augmented Reality System in Simulation and Training", IITSEC, Florida, Dec. 2003.
Brown D., Julier S., Baillot Y. (2003) "An Event-Based Data Distribution Mechanism for Collaborative Mobile Augmented Reality and Virtual Environments", Proceedings of VR2003, Los Angeles, Mar. 2003.
Brown D., Julier S., Baillot Y., Livingston M., Rosenblum L. (2004) "Event-Based Data Distribution for Mobile Augmented Reality and Virtual Environments", Presence: Teleoperators and Virtual Environments, vol. 13, Issue 2, Apr. 2004.
Davis, L., Rolland, J.P., & Baillot, Y. (1998) "Probe design for Tracking Based on LED imaging", CREOL/UCF, Technical Report 98-03.
Foxlin E., Altshuler Y., Naimark, L. Harrington M. (2004) "Flight-Tracker: A Novel Optical/Inertial Tracker for Cockpit Enhanced Vision", IEEE/ACM ISMAR 2004, Washington D.C. Nov. 2004.
Foxlin E., Naimark, L. (2003) "Miniaturization, Calibration & Accuracy Evaluation of a Hybrid Self-Tracker", IEEE/ACM ISMAR 2003, Tokyo, Oct. 2003.
Foxlin, E. (2000) "Head-tracking relative to a moving vehicle or simulator platform using differential inertial sensors", Proceedings of Helmet and Head-Mounted Displays V, SPIE vol. 4021, AeroSense Symposium, Orlando, FL, Apr. 2000.
Gabbard J., Hix D., Swan E., Livingston M., Hollerer T., Julier S., Brown D., Baillot Y. (2003) "Usability Engineering for Complex Interactive Systems Development", HSIS 2004, Viannn, VA, Jun. 2003.
Hix D., Gabbard J., Swan II E., Livingston M., Höllerer T., Julier S., Baillot Y., Brown D (2004) "A Cost-Effective Usability Progression for Novel Interactive Systems", HICSS 2004, Hawaii, Jan. 2004.
Höllerer T., Feiner S., Hallaway D., Bell B., Lanzagorta M., Brown D., Julier S., Baillot Y. and Rosenblum L. (2001) "User interface management techniques for collaborative mobile augmented reality", Computers & Graphics, vol. 25, Issue 5, Oct. 2001, pp. 799-810.
Julier S., Baillot Y., Lanzagorta M., Rosenblum L. and Brown D. (2001) "Urban Terrain Modeling for Augmented Reality Applications", In M. Abdelguerfi (Ed.), 3D Synthetic Environments Reconstruction (pp. 119-136). Dordrecht, The Netherlands: Kluwer Academic Publishers 2001.
Julier S., Brown D., Baillot Y. (2001) "The need for AI: Intuitive User Interfaces for Mobile Augmented Reality Systems", AIMS2001, Seattle.
Julier S., Lanzargota M., Baillot Y., Brown D. (2002) "Information Filtering for Mobile Augmented Reality", 2002, IEEE CG&A.
Julier, S., Baillot, Y., Lanzagorta, M., Brown, D., Rosenblum, L. (2000) "BARS: Battlefield Augmented Reality System", NATO Symposium on Information Processing Techniques for Military Systems, Istanbul, Turkey, Oct. 9-11, 2000.
Julier, S., Lanzagorta, M., Baillot, Y., Rosenblum, L., Feiner, S., Höllerer, T., Sestito, S. (2000) "Information Filtering for Mobile Augmented Reality", Proceedings IEEE International Symposium on Augmented Reality 2000, Oct. 5-6, Munich, 3-11.
Livingston M., Brown D., Swan II E., Goldiez B., Baillot Y., Schmidt G. S. (2005) "Applying a Testing Methodology to Augmented Reality Interfaces to Simulation Systems", Western Simulation Multiconference (WMC '05), New Orleans, LA, Jan. 23-27, 2005.
Livingston M., Rosenblum L., Julier S., Brown D., Baillot Y., Swan E., Gabbard J., Hix D. (2002) "An Augmented Reality System for Military Operations in Urban Terrain", IITSEC, Florida, Dec. 2002.
Livingston M., Swan E., Gabbard J., Höllerer T., Hix D., Julier S., Baillot Y., Brown D.(2003) "Resolving Multiple Occluded Layers in Augmented Reality", ISMAR 2003, Tokyo, Oct. 7-10. Tokyo, Japan.
Memi, E. (Nov. 2005), "Boeing celebrates five years of continuous human presence on ISS", Boeing Frontiers Online, printed from http://www.boeing.com/news/frontieres/archive/2005/november/i_ids1.html.
Naimark L., Foxlin E., "Encoded LED System for Optical Trackers", InterSense Inc., (4 pp.).
Nash, J. (Oct. 1997), "Wiring the Jet Set", printed from http://www.wired.com/wired/5.10/wiring_pr.html on Mar. 30, 2006 (2 pp.).
Rolland, J.P., Y. Baillot, and A. Goon (2000) "A survey of tracking technology for virtual environments", in Augmented Reality and Wearable Computers. Ed. Barfield and Caudell (Mahwah, NJ), (2000).
Rolland, J.P., Y. Baillot, L. Davis, L. Vaissie, and Wright D.L. (1998) "Role of optics in virtual environments" Invited, Proceeding of the International Lens Design Conference, Hawaii.
Schmidt G., Brown D. G., Tomlin B. E., Swan II E., Baillot Y. "Toward Disambiguating Multiple Selections for Frustum-Based Pointing", VR2006, 3DUI Symposium, Washington DC, 2006.
Schmidt G., Brown D. G., Tomlin E. B., Swan II E, Baillot Y. Probabilistic Algorithms, Integration, and Empirical Evaluation for Disambiguating Multiple Selections in Frustum-Based Pointing. Journal of MultiMedia (JMM) 2006, Sep. issue.
Simon Julier, Mark A. Livingston, J. Edward Swan II, Yohan Baillot, Dennis Brown, "Adaptive User Interfaces in Augmented Reality", In Proceedings of the Workshop on Software Technology for Augmented Reality Systems, at the International Symposium on Mixed and Augmented Reality (ISMAR '03), Oct. 7-10, 2003, Tokyo, Japan.
Swan II E., Livingston M. A., Smallman H. S., Brown D., Baillot Y., Gabbard J. L, Hix D., "A Perceptual Matching Technique for Depth Judgments in Optical, See-Through Augmented Reality", Technical Papers, Proceedings of IEEE Virtual Reality 2006, Alexandria, Virginia, USA, Mar. 25-29, pp. 19-26.
International Search Report and Written Opinion mailed Sep. 2, 2008 in PCT/US07/11288.
International Search Report and Written Opinion, mailed Jul. 28, 2008 in PCT application PCT/US08/03037.
U.S. Appl. No. 11/715,338—Apr. 16, 2009 PTO Office Action.
U.S. Appl. No. 11/715,338—Sep. 2, 2009 PTO Office Action.
U.S. Appl. No. 11/715,339—Apr. 2, 2010 PTO Office Action.
U.S. Appl. No. 11/715,338—May 12, 2010 PTO Office Action.
U.S. Appl. No. 11/715,339—Jun. 22, 2010 PTO Office Action.
AU Appln. No. 2007268122—Mar. 7, 2011 IP Australia Examiners Report.
AU Appln. No. 2008226931—Mar. 9, 2011 IP Australia Examiners Report [2 pages].
International Preliminary Report on Patentability in PCT Appln. No. PCT/US2008/003037, dated Sep. 8, 2009.
International Search Report and Written Opinion in PCT Appln. No. PCT/US2008/003037, mailed Jul. 28, 2008.
International Preliminary Report on Patentability in PCT Appln. No. PCT/US2007/011288, dated Nov. 27, 2008.
AU Appln. No. 2008226932 201104-04 IP Australia Examiner's Report [2 pages].
International Preliminary Report on Patentability in PCT Appln. No. PCT/US2008/003038, dated Nov. 17, 2009.
International Search Report and Written Opinion mailed May 15, 2009 in PCT/US2008/003038.
Supplementary Search Report in EP Appln. No. 08726549.2, mailed May 2, 2011.
EP Appln. No. 08726548.4—Dec. 1, 2011 EPO Search Report.
Koeda, Masanao, et al., "Annotation-Based Rescue Assistance System for Teleoperated Unmanned Helicopter with Wearable Augmented Reality Environment," International Workshop on Safety, Security and Rescue Robotics; Kobe, Japan, Jun. 6, 2005, pp. 120-124.
Extended European Search Report mailed Aug. 16, 2011 in EP Appln. No. 07776950.3.
JP Appln. No. 2009-513161—Aug. 15, 2011 JIPO Notice of Reasons for Rejection.

(56) References Cited

OTHER PUBLICATIONS

Nakagawa et al., "Development of Maintenance Support System by Using Image-Based Augmented Reality", materials for seminars of the Institute of Electrical Engineers of Japan, Japan, the Institute of Electrical Engineers of Japan, Sep. 9, 1998, pp. 19-24.
U.S. Appl. No. 11/715,338—Aug. 29, 2011 PTO Office Action.
Welch G. et al.: "Motion tracking: no silver bullet, but a respectable arsenal", IEEE Computer Graphics and Applications, IEEE Service Center, New York, NY, US vol. 20, No. 6, Nov. 1, 20002, pp. 24-38, XP011201226, ISSN: 0272-1716.
EP Appln. No. 07776950.3—Jan. 18, 2012 EPO Office Action.
EP Appln. No. 08726548.4—Dec. 20, 2011 Supplementary European Search Report.
JP Appln. No. 2009-513161—Jan. 16, 2012 JIPO Notice of Final Rejection (with English Translation).
U.S. Appl. No. 11/715,338—Oct. 1, 2015 PTO Office Action.
AU 2007268122—Jan. 25, 2012 APO Examination Report.
CA Appln. No. 2,579,371—May 26, 2014 CA Office Action.
CA Appln. No. 2,679,371—Apr. 12, 2013 CIPO Office Action.
CA Appln. No. 2,679,427—Office Action dated Aug. 22, 2014.
CA Appln. No. 2,679,427—Office Action dated May 20, 2015.
EP 07776950—Communication dated May 20, 2015.
EP Appln. No. 07776950.3—Jan. 21, 2013 EPO Office Action.
EP Appln. No. 07776950.3—Mar. 5, 2013 EPO Office Action.
JP Appin. No. 2009-552743—Feb. 13, 2013 Official Action (with English translation), JPO.
JP Appln. No. 2009-552743 Office Action (w/English translation) mailed Nov. 29, 2013.
U.S. Appl. No. 11/715,338—Mar. 27, 2012 PTO Office Action.
U.S. Appl. No. 11/715,338—Jun. 12, 2014 PTO Office Action.
U.S. Appl. No. 11/715,338—Mar. 24, 2015 PTO Office Action.
U.S. Appl. No. 13/354,167—Mar. 4, 2013 PTO Office Action.
U.S. Appl. No. 13/354,167—Dec. 24, 2013 PTO Office Action.
U.S. Appl. No. 13/354,167—Sep. 16, 2014 PTO Office Action.
U.S. Appl. No. 13/354,167—Jul. 9, 2015 PTO Office Action.

* cited by examiner

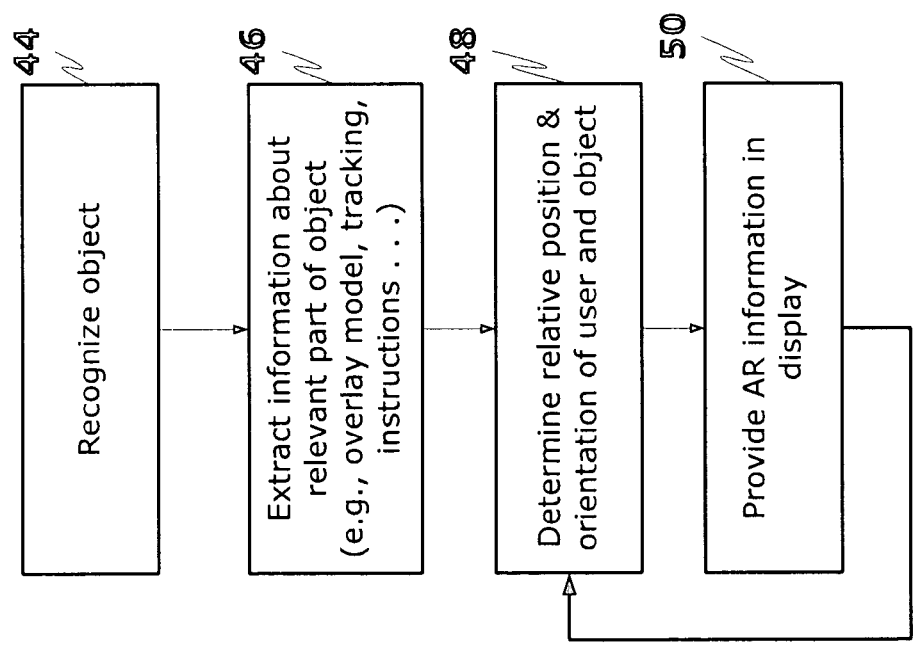

SYSTEM AND METHOD TO DISPLAY MAINTENANCE AND OPERATIONAL INSTRUCTIONS OF AN APPARATUS USING AUGMENTED REALITY

FIELD OF THE INVENTION

This relates generally to an augmented reality (AR) system, and, more particularly to an AR system for displaying maintenance and/or operational instructions of an object.

BRIEF DESCRIPTION OF THE DRAWINGS

For a more complete understanding of the present invention and the advantages thereof, reference should be made to the following detailed description taken in connection with the accompanying drawings, in which:

FIG. 3 is a flowchart of the operation of an AR system.

Figure 1:
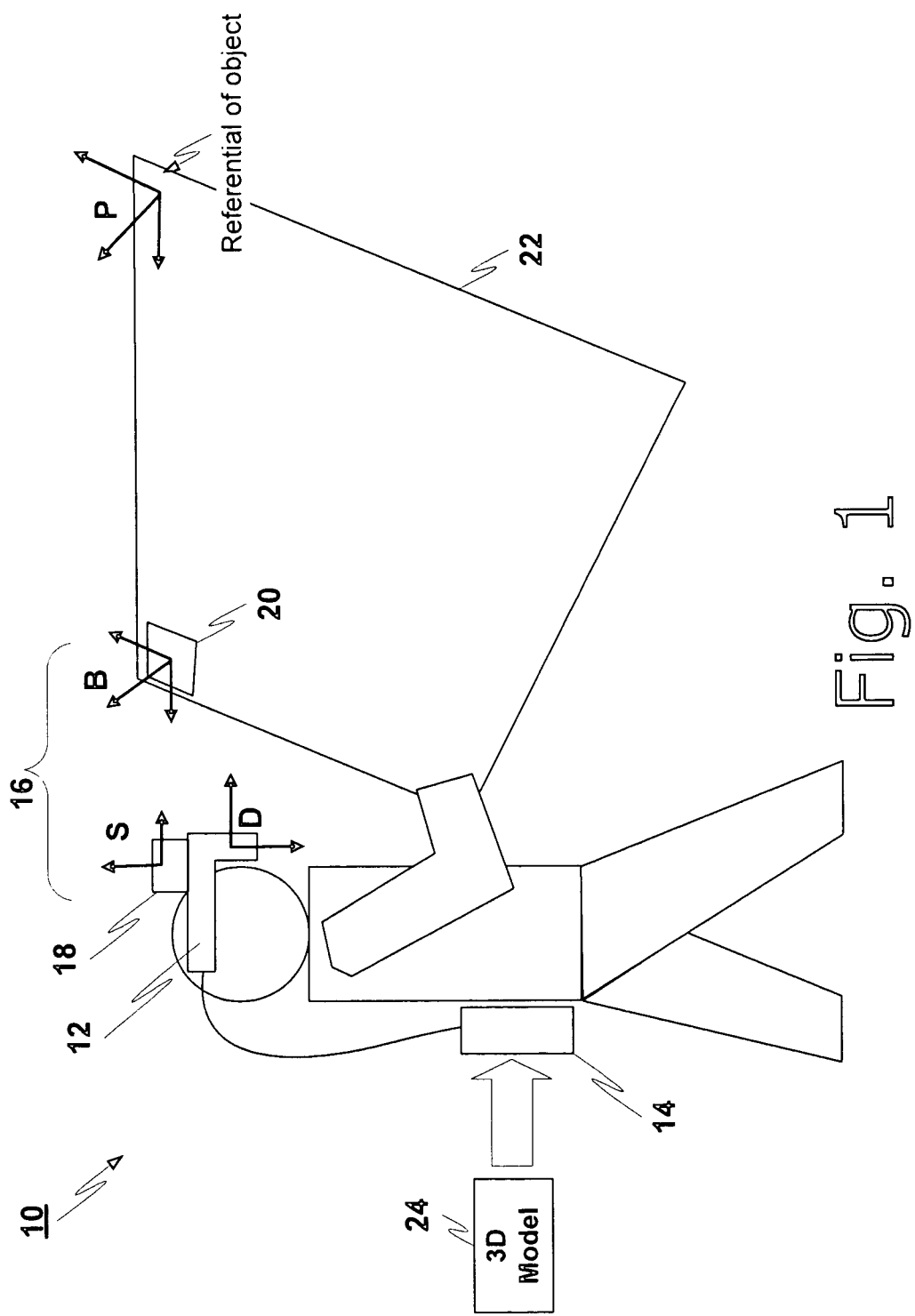
FIG. 1 shows the exemplary architecture of an augmented reality system.

DETAILED DESCRIPTION OF THE PRESENTLY PREFERRED EXEMPLARY EMBODIMENTS OF THE INVENTION

Introduction And Background

Augmented Reality (AR) systems are systems that combine information (e.g., images, text and the like) on views of real-world objects, thereby augmenting the reality (i.e., the real world objects) with other information.

A well known example of an AR system is one used in televised American football to display a yellow line on top of a real-world video image of football field during a football game. This yellow line provides viewers with an indication of the position of the first down marker. Another sports-world example is found in Olympic swimming and track events, where an athlete's country flag is superimposed on the image of that athlete's lane or track. In this way, television viewers can tell which athlete is in which lane.

In some systems, it may be desirable to know the position of a user within a system or framework or relative to one or more objects within a system. As used herein, with reference to a user, the term "tracking" generally refers to the acquisition of the user's position and orientation relative to a coordinate system. A user's position and/or orientation may be determined/tracked in one of two general ways, generally referred to as "inside out" or "outside in" determination. In an "inside-out" tracking system, targets are positioned in known fixed locations (e.g., on the ceiling of a room). A camera connected to or worn by a user obtains images of the targets, and the user's position and/or orientation is determined by a computer connected to the camera. (The term "pose" is sometimes used to refer to an object's (or user's) position and orientation.) The camera may be on a helmet worn by the user. The camera should be attached rigidly to the display because it serves the purpose of sensing the pose of the display so that images can be displayed accordingly. In so-called "outside-in" tracking systems, a user wears so-called targets, and cameras at known, fixed locations are used to detect those targets. Images from the cameras are used to compute the user's location and/or orientation. A combination of these two tracking systems, so-called "inside-outside-in" tracking is also known. It is also known to use active and/or passive targets for the various kinds of tracking systems (e.g., in determining the exact position of a pilot's head—actually helmet—in a plane's cockpit). Other tracking systems use global positioning systems and the like to obtain a user's position (but not orientation), and compasses and the like to obtain a user's orientation (but not position).

Some AR systems have proposed the use of tracking to determine a user's position, e.g., at an archeological site. In these systems, an arbitrary reality is provided to the user using, e.g., a wearable computer and a see-through head-mounted display (HMD). In such systems, tracking can be done using a global positioning system (GPS) combined with other tracking schemes.

Head-mounted optical displays have been used to provide computer-generated information to users, but the information is displayed in a fixed location on the display, and does not change when the user's view of an object changes. For example, a system is known that displays circuit diagrams and the like to users in of a mono-vision head mounted display. But the displayed information is not in any way synchronized with any object that the user is viewing, and if the user moves (thereby changing his view of the object), the information does not move at the same time with respect to the display in such a way that it would appear attached to specific objects in the environment.

The inventors were the first to realize the desirability of combining head-mounted displays with precise and continuous position and orientation tracking to provide overlaid maintenance and operation instructions to users under potentially difficult conditions, including onboard a ship, in darkness, surrounded by metal and other surfaces, and with limited space.

DESCRIPTION

FIG. 1 depicts an exemplary architecture of an augmented reality (AR) system 10. The AR system 10 includes a head-mounted display 12 connected to a computer 14.

The computer 14 is preferably light-weight and wearable, so that its use does not unduly impinge on a user's mobility. In a presently preferred implementation, the computer 14 is a wearable x86 clone from Quantum3D called the Thermite. This computer is low powered, rugged, has a 1 GHz processor and 256 Mb of memory, and an Nvidia graphic adapter that is appropriate for real-time monocular AR graphics rendering. Those skilled in the art will realize and understand, upon reading this description, that different and/or other computers may be used. The display 12 may be connected, e.g., to the VGA output of the computer 14. The system 10 may also include a keyboard or the like (not shown) for use as an input device.

The display 12 is a see-through display that allows for augmentation of the user's view. The display can either be transparent (optical) or non-transparent (video based). Video based see-through displays may be implemented by a camera taking a view of the world. Video based displays show this view of the world combined with graphics that augment the view. Optical displays may be implemented, e.g., by showing the view of the world through a transparent beam-splitter and combining this view with the graphics augmenting the view by reflecting a micro-display display image showing this graphics using the same beam-splitter. See-through displays are available in the form of goggles that can be worn by a user for better immersion of the user in the AR. The optical and video displays can be either monoscopic (one view) or stereoscopic (two views, one for each eye) to support depth perception. The later kind is recommended for a better matching of the virtual and real image. An example of a monocular, see-through, non-obstructive optical display is the Nomad II display available from Microvision of Redmond, Wash.

The Microvision Nomad II display is also appropriate because it is light, wireless, and can be used under any lighting conditions. It uses a laser to form a high intensity image on the wearer's eyes and therefore can be made bright enough to compensate for ambient lighting conditions. The display has a common VGA port that can be used to send images. A binocular display with the same characteristics as the Nomad II may be preferable, since it has been suggested that users may experience attention shift when using monocular display.

In order for a user to determine what is being viewed (so that information about that object can be provided) the system 10 determines the user's position and/or orientation with respect to an object being viewed. To this end, the AR system 10 includes a tracking system 16 which is made up of a tracking mechanism/device 18. The tracking mechanism 18 can be one or more cameras, although other mechanisms may be used. For the purposes of this description, the terms "tracking mechanism" and camera are used synonymously. It is generally desirable the tracking mechanism 18 be in a known and fixed position and orientation with respect to the head-mounted display 12.

The tracking system 16 also includes at least one marker (or beacon) 20 on the object to be viewed. Preferably more than one marker is provided, although, for the sake of explanation, only one marker is shown on the object 22 in the drawing.

A typical AR system 10 will operate in an environment in which there is a plurality of different objects 22.

The marker(s) 20 may be placed on, attached to, or built into the object 22. In presently preferred embodiments, the marker 20 is preferably an active marker—e.g., a source that produces infrared (IR) or ultra-violet (UV) light. Marker 20 may use IR or UV radiation sources that create a geometric pattern that can be seen by the imaging sensor of tracking mechanism 18 and segmented/distinguished from the rest of the scene by a tracking system processor. Marker 20 may include IR light-emitting diodes (LEDs) that create points or beacons on the imaging plane of the tracking mechanism 18. UV LEDs could be used instead, or similarly lines or arbitrary shapes could be created instead of points. The pattern created by the marker 20 should be rotation invariant, and may be asymmetric, so that the tracking system 16 can find only one solution to the position and orientation (or pose of the tracking mechanism 18). When IR or UV LEDs are used for markers 20, the LEDs may be constantly on and provide reliable targets that can be segmented by the camera regardless of arbitrary ambient illumination. Markers 20 may be battery powered or hardwired into the apparatus 22 in order to obtain their power.

In addition to IR LED markers 20, the tracking system 18 may also use UV sources or laser targets emitting IR or UV as markers that can provide beacons that a tracking mechanism (e.g., camera) can view and that cannot be seen by a human.

It should be understood that the term "marker" may refer to one or more marks or patterns or LEDs. That is, a particular, individual marker may comprise one or more marks, patterns or LEDs. The pattern formed by a marker is referred to as the marker's constellation.

An alternative tracking system can be implemented using retro reflecting targets for markers instead of point sources. Such a system would require an illumination mechanism (e.g., an IR flash), preferably placed on the same axis than the tracking mechanism 18. In such a system, the tracking system 16 illuminates the reflecting target with the illumination mechanism, and the reflected targets appear to the optical detector as if they were light source themselves, providing the same function.

The tracking mechanism 18 is preferably a lightweight camera that is attached to display 12. The camera preferably uses an imaging sensor operating in a frequency range that is invisible to humans, e.g., either IR or UV. Examples of implementation of the imaging sensor are a CCD (charge coupled device) included in the camera or two linear optical sensors. Those skilled in the art will realize and understand, upon reading this description, that other embodiments supporting the same imaging functions can also be used. Since the tracking system 16 uses active (as opposed to passive) light sources, it is not sensitive to ambient lighting conditions.

Additionally, the tracking mechanism 18 (e.g., camera) can include one or more filters (e.g., an IR filter) to filter out ambient illumination and help in segmentation.

The tracking system 16 may generate tracking information by determining the position and orientation of the tracking mechanism 18 with respect to the marker 20 (referred to herein as the BS—Base-to-Sensor—orientation) and/or the position and orientation of the marker 20 with respect to the tracking mechanism 18 (referred to herein as the SB—Sensor-To-Base—orientation), depending on its implementation. Since the tracking system 16 tracks the relative position and orientation of the tracking mechanism 18 and marker 20, the AR system 10 is able to overlay images on the object 22, even when the position and/or orientation of the object changes (so long as the marker 20 remains attached to the object).

The optical-based tracking may be implemented using a well-known algorithm which consist on correlating the projected position of the markers 20 (e.g., IR LEDs) on the imaging sensor of the tracking mechanism 18 with their corresponding known spatial location on the object 22. This allows recovery of the position and orientation of the tracking mechanism 18. This aspect of the AR system may be implemented using a so-called model-based pose recovery algorithm. A bibliography of such algorithms is provided, e.g., at the University of Rochester Computer Science Department Web site (http://www.cs.rochester.edu/u/carceron/research/bib.html).

The tracking system 16 may be implemented, alternatively, using an inertial sensor (not shown) on the tracking mechanism 18 and marker 20 to reduce the processing power required by the system. The use of inertial sensors in position tracking is well-known, and is described, e.g., in "Head-tracking relative to a moving vehicle or simulator platform using differential inertial sensors," Foxlin, *Proceedings of Helmet and Head-Mounted Displays V, SPIE Vol.* 4021, AeroSense Symposium, Orlando, Fla., April 24-25, 20, and U.S. Pat. Nos. 6,474,159; 6,757,068, and 6,922,632, the entire contents of each of which are incorporated herein by reference.

Inertial information may be used to allow the segmentation function of the algorithm to be done only in small regions (search windows) of the tracking mechanism, instead of scanning the whole image. The underlying mathematical principle to determine the position and orientation of the tracking mechanism 18 with respect to marker 20 is the same once the marker 20 has been segmented on the imaging sensor of the tracking mechanism.

In presently preferred embodiments, the object 22 is an apparatus (e.g., an instrument panel) requiring repair or maintenance. Further, in presently preferred embodiments, the object 22 is on board a moving vessel such as ship at sea or the like. Those skilled in the art will realize and understand, upon reading this description, that in such cases, both the user and the object will be moving relative to each other at all times. In addition, in such cases, the AR system 10 will have to deal with differing light conditions (e.g., ambient light, noise reflections that look like LEDs, poor visibility and possibly darkness).

The inventors realized that for various reasons, including for cost reasons and to respect the constraint that there are likely more objects 22 to be annotated/marked than users, the tracking system 16 is preferably of the inside-out type. This means that the tracking processing and the tracking mechanism 18 are carried by the user and the markers are mounted in the environment rather than the reverse, outside-in configuration.

It is desirable that the optical detector of the tracking mechanism 12 has a large field of view so that as the user gets closer to an object, enough markers can be seen. An alternative approach would be to use a denser marker distribution on the object.

The tracking system 16 may use the computer 14 (or some other processor—not shown) to run needed algorithms and help in determining the position and orientation of tracking mechanism (camera) 18 with respect to marker(s) 20 or the orientation of marker(s) 20 with respect to respect tracking mechanism (camera) 18, depending on the implementation. Alternatively, a dedicated processor or embedded hardware can perform some or all of this functionality.

Once the tracking system 16 has generated tracking information, this information is used to infers the position and orientation of the display 12 with respect to the object 22 that the user is looking at (this information is referred to herein as PD—Panel-to-Display).

For each object that might need to be viewed (repaired, maintained, etc.), a three-dimensional (3D) model 24 of the object 22 is created (e.g., using a 3D model or an image or arbitrary coordinates obtained by surveying) and is stored in the computer 14 before the user operates the system. This model 24 is referenced with respect to the object 22. Using the position and orientation of the display 12 with respect to the object 22 and the 3D model 24 of the object 22, the computer 14 is able to generate a perspective of the 3D model and to render the perspective to superimpose overlay information on the object 22 and send the corresponding overlay image to the display 12. In this manner, the user can see an overlay image of the object (in the display 12) while viewing the object. Since the tracking is preferably continuous and on-going, if the user and/or the object move with respect to each other, the overlay image is displayed in the correct place.

As noted above, in presently preferred embodiments, the object 22 is an apparatus/device (e.g., an instrument panel), e.g., on board a moving vessel such as ship at sea or the like. The information provided in the overlay image includes information about the apparatus and/or its maintenance and/or repair. So, for example, a user looking at an appropriately marked instrument panel may be provided with an overlay image giving operation and maintenance instructions directly superimposed on the instrument panel. It is important that the overlay image be correctly positioned on the object being viewed. It should thus be apparent to those of skill in the art, from reading this description, that if either the user or the object move, it will be necessary to update the overlay image to ensure that it corresponds to the correct parts of the real-world object being viewed.

In preferred embodiments, the information provided to the user includes equipment repair and/or maintenance instructions.

The information to be used in the augmented display may be obtained from a database stored in the computer 14 or stored remotely and accessed (e.g., wirelessly) by the computer as needed. Interaction between the computer 14 and the database can use any known technique.

Figure 2:
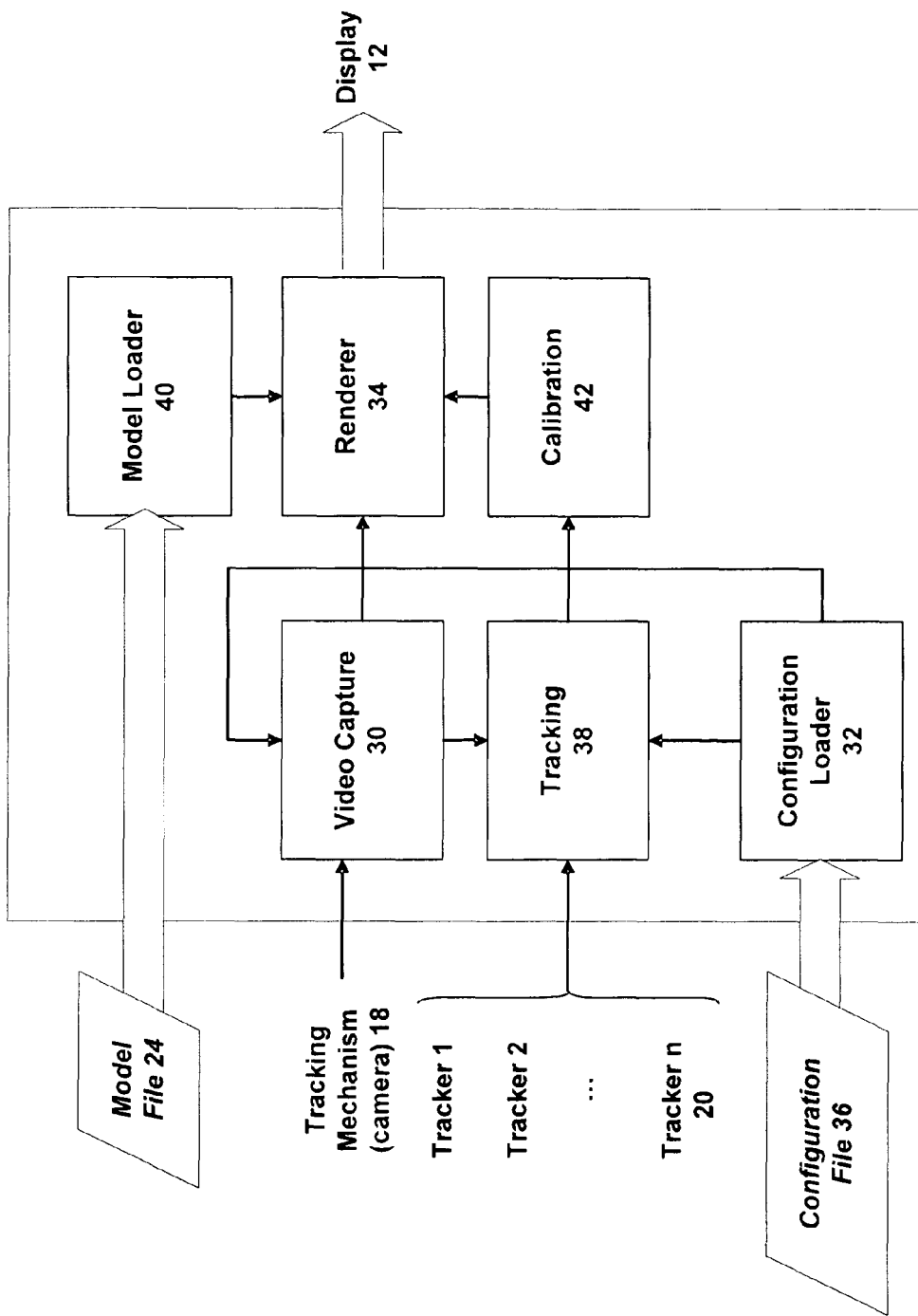
FIG. 2 shows the exemplary AR architecture.

FIG. 2 depicts an exemplary architecture of the video AR system 10. Those skilled in the art will realize and understand, upon reading this description, that this architecture can be implemented in hardware or software or combinations thereof. In addition, those skilled in the art will realize and understand, upon reading this description, that other and or different architectures may be used. In some embodiments, different cameras could be used for the AR view and for the tracking. Additionally, an optical AR system can be used, in which case the video does not go to the renderer (since the real world can be seen through the transparent optics).

As shown in FIG. 2, an exemplary architecture includes a video capture section 30, a configuration loader 32, a renderer 34, a tracking section 38, a model loader 40, and a calibration mechanism 42. A configuration file 36 is used to configure the tracking section 38 of the software and the tracking mechanism 18 (camera). The configuration file 36 provides data (e.g., locations of the tracking LEDs with respect to the referential to track, here the machine origin) needed by the tracking system 16. The configuration loader 32 reads the configuration file 36. Those skilled in the art will realize and understand, upon reading this description, that the configuration data may be provided in any number of formats and via different mechanisms than those shown.

Calibration section 42 calibrates the transformation between 18 and the display 12, if and as necessary. Tracking section 38 provides information about the markers 20 (including the pose of the camera with respect to the marker constellation) that are in the environment. Video processing section 30 connects to the tracking mechanism 18 (camera), and provides video input for tracking. Video processing section 30 may also be constructed and adapted to perform various functions such as to compensate for lens distortion and the like, e.g., by using inverse-distortion mapping; to provide video texture capabilities; and to capture video frames that represents that user's view (in the case of a video-see-through, where a video camera take a view of the real world).

Model loader 40 loads model files 24 associated with an object in the environment. In video-see-through mode, renderer 34 receives the video input from the video processing section 30 and the position and orientation of the display 12 with respect to the object from tracking 16.

The tracking section 38 and calibration section 42 are constructed and adapted to determine the position and orientation of the display 12 with respect to an object which is referred to as PD (panel-to-display). In presently preferred embodiment, the renderer 34 uses the transformation (PD) which calculation is based, at least in part, on the following well-known relationship: a point imaged on the optical detector plan Pd is related to its location on the object to track Po by the matrix equation:

$$Pd = P \cdot Tdo \cdot Po$$

where Tdo is the matrix changing the coordinates of the marker(s) 20 from the referential of the object 22 to the tracking mechanism 18, and P is the projection matrix of the tracking mechanism 18, expressing the manner in which the optics project the point on the detector plane of the tracking mechanism 18. Because Po (the location of a LED or beacons with respect to the origin of the object 22), P (the projection matrix defined by the optics of the camera 18) and Pd (the 2D projected blob produced by the LED or beacons on the image plane of the camera) are known, it is possible to determine Tdo (the tracking transform). The matrix Tdo also encodes the translation and rotation needed to map from the tracking mechanism 18 to the object 22 (in essence the pose of the object 22 with respect to the tracking mechanism 18), hence providing the tracking capability. By reverting the transforms, the tracking mechanism 18 can also be tracked with respect to the object 22. PD is computed using the computed transform Tdo combined with the TD transform from the tracking 18 to the display 20, in order to get the object 22 to display 12 transform OD.

Once the renderer 34 has the position and orientation of the display 12 with respect to the object 22, the renderer 34 uses this information and model information (from 3D model file 24) from the model loader 40 to generate the appropriate overlay information. The renderer 34 then sends overlay information to the display 12.

In some embodiments, a bar code or other indicia may be used in conjunction with the markers to provide the AR system with initial information about the object being viewed. While it should be understood that such indicia may not always be available or visible, they may provide useful startup information and may therefore be used to speed up initial object recognition. Initial object recognition is desirable for scalability and individual motion of the objects to augment with respect to each other. The object recognition allows one to configure the tracking so that it only has the constellation of LEDs that is needed for this object, thereby to reduce processing time and improve scalability. If this approach is not taken, a global constellation can be used for all objects. However, performance of the tracking will decrease as the number of object grows. Those skilled in the art will recognize several possible way to implement this recognition step. One implementation is to configure the tracking system with the constellation for all machines (called the global constellation) at initialization or when the user moves away from a specific machine (detected by the tracking). When using the global constellation, the tracking produces a position which maps to a specific machine position in the global constellation frame of reference. Once this machine is identified, the tracking can then be configured with the sub-constellation which is only for the machine of interest. Another implementation consists of using a rough tracking system such as an RFID or the like attached to each machine allow the AR system to recognize the machine of interest.

Since, as noted above, the AR system 10 may be used in all sorts of environments, including for maintenance and repair of complex systems on board ships and the like, those skilled in the art will realize and understand, upon reading this description, that the user of such a system may be viewing an object to be repaired from an unpredictable angle and/or location. In cases where a bar code or other indicia are provided, the system would be able quickly to determine which of many possible objects is being viewed. Additionally (or alternatively) the spatial arrangement of the beacons or LEDs can be used as an indicia. For example, a square=1, a triangle=2 and so on.

In some embodiments, the marker(s) 20 may comprise active LEDs which encode, e.g., in some modulated form, a signal providing an identification of the object. Again, such information may allow for quicker recognition of the object by the AR system.

In yet other embodiments, the user may be provided with a keyboard or the like with which to enter initial configuration information such as, e.g., an identification of the object under view.

Those of skill in the art will realize and understand, upon reading this description, that a computer-generated image, overlaying a real-world view of an object, will move when the object and/or user move relative to each other. In this manner, the graphics will appear to the user to stay in place on the real world object. This updating of the computer-generated image preferably occurs continuously. Those skilled in the art will understand, upon reading this description, that the term "continuously", as used herein, means repeated in a continuous manner. The actual appearance of the computer-generated image may appear jerky or discontinuous if the user and the object are moving a lot with respect to each other. In such cases, the computer system may not be able to keep the image precisely updated at all times.

FIG. 3 is an exemplary flowchart of the operation of the AR system of FIG. 1. As shown in FIG. 3, first the system recognizes the object being viewed (at 44). This recognition may be performed by looking at the constellation formed by the marker(s), as described above, or using image recognition or some other approach.

Next, information about the object being viewed is obtained (e.g., from a database) (at 46). This information can consist, e.g., of an up to date model to overlay on the machine, some updated instruction, the tracking configuration to employ.

The system then determines the relative position and orientation (i.e., the pose) of the user (actually, the tracker/display) relative to the object (at 48), and displays appropriate information to the user (at 50). The user's position/orientation with respect to the object is continuously tracked, and steps 48-50 are repeated as necessary.

Those skilled in the art will realize and understand, upon reading this description, that some or all of these initial recognition techniques may be used in combination, and further, that different and/or other techniques may be used with initial object recognition.

Among its many advantages, the present system does not rely on previously-seen views to infer incremental changes in position and orientation. Instead, in preferred embodiments, current position and orientation are recomputed each time. This approach allows the system to cope with problems associated with occlusion (which are encountered by system operating on prior information).

Those skilled in the art will realize and understand, upon reading this description, that the AR system described herein overcomes deficiencies in current AR systems. An AR system as described has one or more of the following advantages:
  it is wearable;
  it is not sensitive to varying or inexistent ambient illumination;
  it is not sensitive to noise;
  it is not sensitive to motion of the object being viewed;
  it is not sensitive to surrounding metal or magnetic field distortions in general;
  it does not need or use wire(s) for synchronization between the user and the object being viewed;
  it does not need or use a tracking reference that is added to the object to be viewed and is visible to human eye;
  it does not rely on previously seen view to infer its incremental change in position and orientation;
  it is light and small enough to be mounted on a user's head.

Those skilled in the art will realize and understand, upon reading this description, that the AR system/framework described has many applications. Some contemplated applications of the AR system include:
  Training for operation and maintenance of fixed or moving instrument or apparatus, e.g.:
    Showing a user how to operate a machine in a plant;
    Showing a user how to use a instrument panel and steering controls in a tank;

Showing a user the function of buttons and flight stick in a plane or helicopter;

Showing a user how to use the instrument panel in a space ship or space station;

Showing a user the function of each buttons on an audio amplifier;

Showing a user how to use something which is not powered except for the power needed for the LEDs, (e.g., a pallet or a weapon), or something that can be carried in the hand or even mounted on the wrist.

In addition, the AR system described may be used to provide information related to an instrument panel or apparatus but that is not for training purpose. For example, using feedback or data from sensors or the like, the AR system may be used to highlight an instrument panel module that requires attention because one of the view meters or buttons of this panel is showing out of normal value. Similarly, the AR system may be used to show actual temperature data inside an enclosed compartment of a machine. For example, a machine's temperature could be determine by a sensor in the machine and displayed on top of the machine using the AR system, giving an indication to the user, perhaps even replacing the indicator with a warning label on the machine itself when looking from far. In this way, a repair person may be provided with additional useful information about an object.

Although the disclosure describes and illustrates various embodiments of the invention, it is to be understood that the invention is not limited to these particular embodiments. Many variations and modifications will now occur to those skilled in the art of augmented reality. For full definition of the scope of the invention, reference is to be made to the appended claims.

What is claimed is:

1. A framework comprising:
   a head-mounted display constructed and adapted to provide a user with an augmented view of a physical object being viewed directly by the user, wherein the physical object is not a digital representation of an object and is one of: (1) an apparatus, (2) a device, (3) an instrument panel and a (2) machine to be one of: (1) maintained and (2) repaired;
   a tracking mechanism constructed and adapted to repeatedly determine the position and orientation of the head-mounted display relative the object being viewed, wherein the tracking system is constructed and adapted to determine its position using a plurality of markers located on the object being viewed; and
   a computer system constructed and adapted to provide one of (1) maintenance and (1) repair instructions displayed overlaid over the user's direct view of the physical object at particular locations relative to the physical object being viewed to create the augmented view and to repeatedly update the augmented view of the physical object being viewed based, at least in part, on the determined position and orientation of the display.

2. A framework as in claim 1 wherein the head-mounted display is a see-through display.

3. A framework as in claim 2 wherein the head-mounted display is selected from: video-based displays and optical-based displays.

4. A framework as in claim 1 wherein the head-mounted display is selected from: monoscopic and stereoscopic displays.

5. A framework as in claim 1 wherein each of the plurality of markers comprises: light-emitting diodes (LEDs).

6. A framework as in claim 5 wherein at least some of the LEDs are selected from infra-red (IR) LEDs and ultra-violet (UV) LEDs.

7. A framework as in claim 5 wherein the LEDs emit invisible light.

8. A framework as in claim 1 wherein the markers are retro-reflective targets, the framework further comprising an illumination mechanism.

9. A framework as in claim 1 wherein the tracking mechanism comprises a camera.

10. A framework as in claim 9 wherein the camera is connected to the head-mounted display.

11. A framework as in claim 9 wherein the camera uses an imaging sensor operating in a frequency range that is invisible to humans.

12. A framework as in claim 11 wherein the frequency is selected from infrared (IR) and ultraviolet (UV).

13. A framework as in claim 1 wherein the tracking mechanism includes one or more filters to filter out ambient illumination.

14. A framework as in claim 1 wherein the object being viewed is selected from a plurality of previously marked objects.

15. A framework as in claim 1 wherein the augmented view of the object presents the information on the object being viewed.

16. A framework as in claim 15 further comprising:
    computer-readable media storing information associated with said plurality of previously-marked objects.

17. A framework as in claim 1 wherein the tracking mechanism is constructed and adapted to substantially continuously determine the position and orientation of the head-mounted display relative to the objected being viewed; and wherein the computer system is constructed and adapted to substantially continuously update the augmented view of the object based on the determined position and orientation of the display.

18. A framework as in claim 1 wherein said instructions comprise condition information about a condition of the object and wherein the augmented display includes that condition information at an appropriate location on the object.

19. A framework as in claim 18 wherein the condition information comprises an internal temperature of the object.

20. A framework as in claim 1 wherein the tracking mechanisms uses an inside-out tracking system.

21. A method in a head-mounted display, comprising:
    Providing a direct view of a physical object to the user, wherein the physical object is not a digital representation of an object and is one of: (1) an apparatus, (2) a device, (3) an instrument panel and a (2) machine to be one of: (1) maintained and (2) repaired;
    repeatedly determining a relative position and orientation of the user with respect to the physical object being viewed by the user, wherein the physical object has a plurality of markers located thereon, and wherein said determining is based at least in part on at least some of the markers; and
    based on said determined position and orientation, repeatedly providing the user with one of (1) maintenance and (1) repair instructions displayed overlaid over the user's direct view of the physical object at particular locations relative to the physical object being viewed to create an augmented view of the physical object being viewed.

22. A method as in claim 21 wherein the steps are repeated substantially continuously.

23. A method as in claim 21 wherein the augmented view of the object provides the information on instructions for the object being viewed.

24. A method as in claim 23 wherein at least one of the particular locations is a location corresponding to a part of the object, and wherein the information is instructions are information relating to that part of the object.

25. A method, in a system having a plurality of actual objects, each of said plurality of actual objects having at least one distinct identification marker associated therewith and having a plurality of position markers associated therewith, the method comprising:
   (a) obtaining an image, said image including a representation of an actual object, said image corresponding substantially with a user's view of the actual object;
   (b) identifying said actual object represented in said image, said identifying being based, at least in part, on at least one distinct identification marker associated with the actual object;
   (c) determining a relative position and orientation of said user with respect to the identified actual object, said determining being based at least in part on at least some of said position markers; and
   (d) providing the user with an augmented view of the actual object,
wherein the augmented view presents one of (1) maintenance and (1) repair instructions displayed overlaid over the user's direct view of the object so as to appear at a specific location relative to a specific part of the actual object.

26. A method as in claim 25 further comprising: repeating steps (a)-(d) at least once.

* * * * *